United States Patent [19]
Handal

[11] Patent Number: 5,263,990
[45] Date of Patent: Nov. 23, 1993

[54] PROSTHETIC WITH BAR REINFORCED SHELL

[76] Inventor: Jady G. Handal, P.O. Box 157, Welcome, Md. 20693

[21] Appl. No.: 803,082

[22] Filed: Dec. 4, 1991

[51] Int. Cl.⁵ ............................................. A61F 2/80
[52] U.S. Cl. ....................................... 623/57; 623/35; 623/33
[58] Field of Search ................................. 623/57-65, 623/33, 35-38

[56] References Cited

U.S. PATENT DOCUMENTS

| | | | |
|---|---|---|---|
| 1,740,230 | 12/1929 | Dorrance | 623/65 |
| 3,889,301 | 6/1975 | Bonner, Sr. | 623/37 |
| 4,016,607 | 4/1977 | Pihlaja | 623/57 |
| 5,139,523 | 8/1992 | Paton et al. | 623/37 |

Primary Examiner—David Isabella
Assistant Examiner—D. Willse
Attorney, Agent, or Firm—Handal & Morofsky

[57] ABSTRACT

A form-fitting residual limb socket or shell comprises, at least in part, a lightweight resinous material. This form-fitting residual limb socket or shell defines a mounting end and an open end. A metal-mounting member is secured to the mounting end and adapted to receive a conventional prosthetic coupling member. A plurality of metal support anchors are secured to the mounting member and extend into the resinous material of the residual limb socket or shell.

19 Claims, 6 Drawing Sheets

PROSTHETIC WITH BAR REINFORCED SHELL

BACKGROUND

Over the years, prosthetic hand replacements have remained substantially unchanged, generally comprising a split hook used to grasp, and/or otherwise handle a work piece or a mechanical hand which includes a two-fingered gripping arrangement.

Likewise, the mounting unit for such artificial devices generally comprises a residual limb socket having a cup at one end. A wrist unit is secured in the cup end. The wrist unit serves as a mounting for the artificial hand or hook.

Residual limb sockets currently in use are comprised of fiberglass or synthetic fiber reinforced plastic or a similar material. These are custom made and very costly. The socket is matched in size and configuration to the residual limb to receive the prosthetic. The match need be so close that a thin fabric stockinette is all that is required between the residual limb and the shell. Naturally the cost of fabrication is extremely high. The closed end of the residual limb socket or shell terminates in a metal mounting member which includes a threaded hole which serves to receive the hand or hook. The hand or hook is kept in position by conventional mechanical means which involve the use of tools which are used to tighten the hand or hook in a firmly fixed angular position in a classic metal to metal tightened joint.

Such prior art devices suffer from numerous inadequacies. More particularly, such prior art devices, due to the fact that their structure is largely made of plastic, will tend to fatigue and break under heavy use. Fatigue also results in a change in the residual limb socket size. As the residual limb socket must be closely matched to the residual limb receiving the prosthetic, fatigue of the plastic residual limb socket results in changing the inner dimension of the residual limb socket, causing a poor fit and in some cases trauma, thus necessitating replacement of even an unbroken residual limb socket or shell. It is noted that while the prior art has stressed the use of various fibers to reinforce the plastic, such reinforcement does not solve the problem of residual limb socket or shell fatigue.

In addition, under use, the cup defined in the closed end of the residual limb socket or shell will tend to break, resulting in the metal mounting member losing its support. Thus, prior art prosthetic devices do not work well for even short periods of time under relatively heavy use, such as that which might be needed by a farmer, auto mechanic, construction worker, or the like.

Finally, even if, at least initially, the shell does not break, heavy use results in severe discomfort due to the relatively hard interface between the residual limb and the socket.

In principle, one could consider several approaches toward solving the above problems. For example, the plastic could be replaced with relatively robust materials, such as steel, but steel would present the problem of extra weight as well as constructional complications insofar as the prosthetic must be custom fitted to each user. Thus, the easy workability of, for example, fiberglass or synthetic fiber reinforced materials, renders them more desirable than metals, because of the object of custom fabrication adapted to the particular user. In addition, a steel prosthetic residual limb socket or shell would be relatively heavy and will change the balance of the device and thus be impractical to use.

While one could, perhaps, address the problem by increasing the diameter of the residual limb socket or shell at its closed end, the structure would be relatively cumbersome to use and unnatural in appearance, although an increased cup size may provide some additional strength. Nevertheless, the amount of improvement which could be achieved by such an artificially large cup size would not be significant.

Still another problem with prior art devices is the fact that tools and highly skilled technicians are needed to fabricate, install and adjust the prosthetic unit.

Moreover, once adjusted, the prosthetic wrist unit of conventional design will not, unless under significant force, easily, adapt to movement outside its initial setting. Thus, for example, if the angular position of a hook is set in the conventional way and the individual is driving a car and a sudden movement necessary to avoid an accident is made, the prosthetic unit will not accommodate that movement well and may result in locking the prosthetic device in the steering wheel and a loss of control.

SUMMARY OF THE INVENTION

The invention, as claimed, is intended to provide a remedy for these problems. It solves the problem of providing an artificial replacement which is at once of normal dimension, rugged construction and lightweight. The same is achieved through the employment of a hybridized residual limb socket or shell which is constructed to be integral with the wrist unit, after assembly of the same, while providing, at the same time, means for nondestructive accommodation of sudden movement. The socket is lined with a foam that acts as a cushion between the residual limb and the hard socket shell, greatly reducing or eliminating trauma and discomfort. This foam liner of the socket also acts to enhance the "pumping" motion which promotes blood circulation in the residual limb. Furthermore, the foam liner can be easily removed and replaced should the residual limb swell or shrink or the foam fatigue. This foam lined residual limb socket is of particular importance in initial prosthetic installation, where limb shrinkage is a major issue often requiring several replacements in the initial two years and in lower limb (legs) prosthetics where the entire body weight of the individual is placed on the residual limb.

Furthermore, women experience a monthly water retention cycle which increases the size of the thigh, for example; this swelling can be easily accommodated with, easily installed and removed, foam liners. The use of an easily inflatable/deflatable air bladder, having a structure similar to that used in pump-up sneakers currently on the market, to adapt the prosthetic foam/socket to periodic swelling has been considered. This bladder is inserted between the foam liner and the hard shell and would obviate the need to change foam liners to accomodate monthly swelling cycles. This will be the topic of future research. Thus added reliability, life and safety is achieved. Moreover the same can be achieved at lower cost than prior art units. At the same time, these objectives are achieved while accommodating improved quality of life, greater comfort and easy replacement of parts, should this become necessary.

BRIEF DESCRIPTION OF THE DRAWINGS

Several ways of carrying out the invention are described in detail below with reference to drawings which illustrate only several specific embodiments, in which.

BEST MODE FOR CARRYING OUT THE INVENTION

Figure 1:
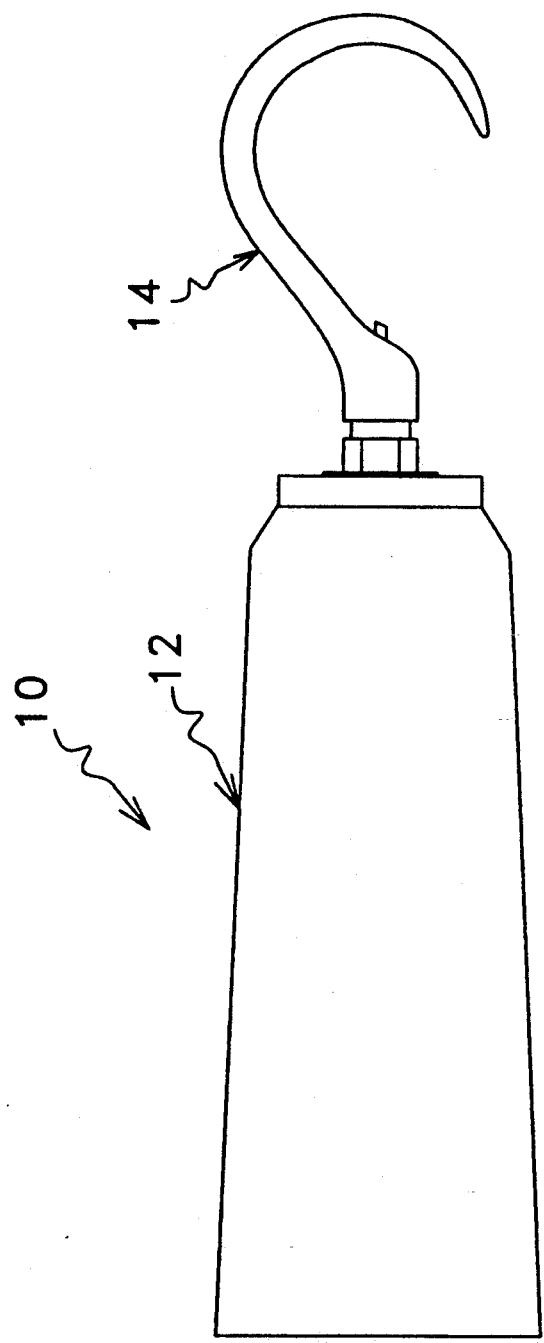
FIG. 1 is a side view of the inventive prosthetic limb device.

Referring to FIG. 1, the prosthetic unit 10 constructed in accordance with the present invention is comprised of residual limb socket or shell 12 and a tool mounted on it such as hook 14.

Figure 2:
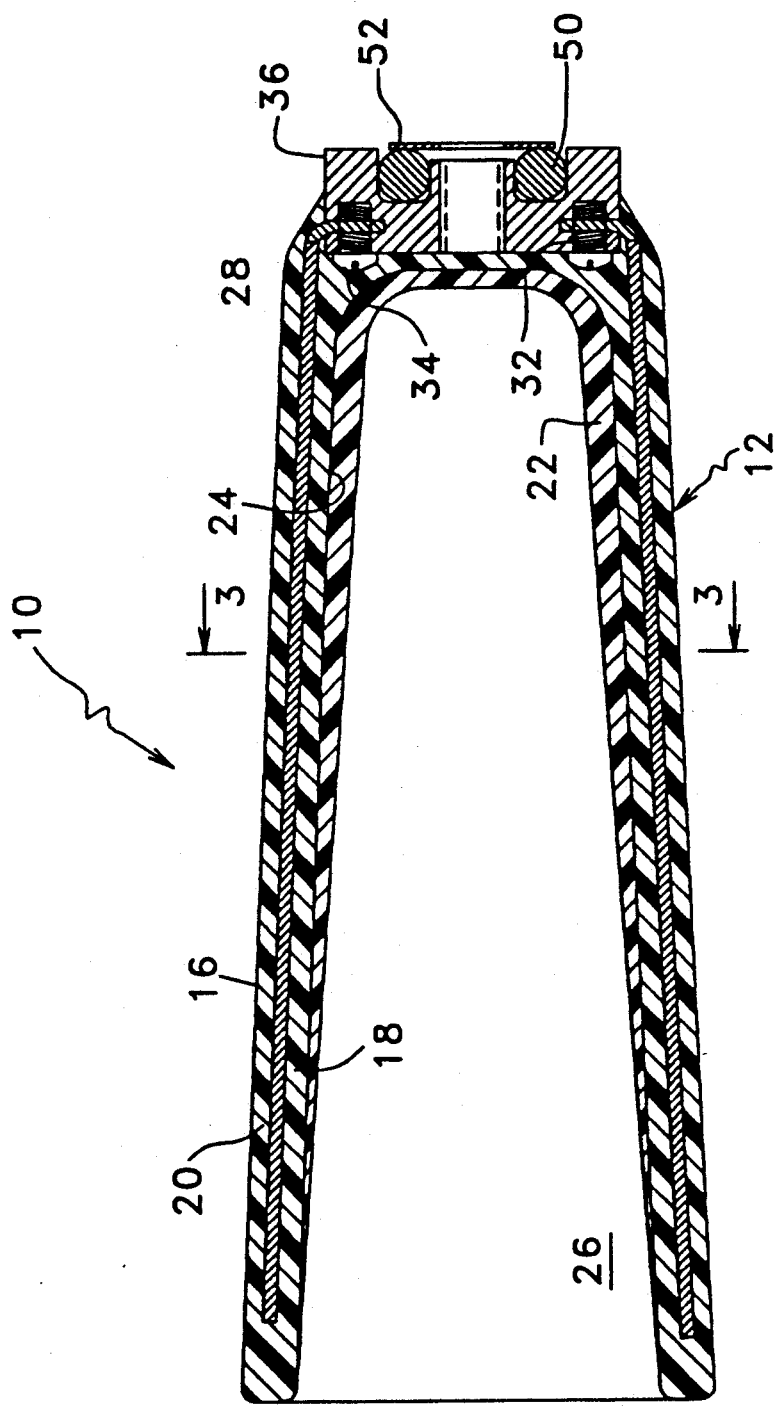
FIG. 2 is a detailed cross sectional view of the device of FIG. 1 without the prosthetic hook.

Referring to FIG. 2, the construction of residual limb socket or shell 12 is illustrated. Generally, residual limb socket or shell 12 comprises a socket member 16 which includes an inner portion 18 and an outer portion 20. A foam fitting member 22 is disposed on the inside of socket member 16, as illustrated most clearly in FIG. 2.

Typically, socket member 16 is comprised of a resinous material reinforced with fiberglass or synthetic fibers. In particular, socket member 16 may be constructed of conventional materials.

Foam fitting member 22 may be made of resilient, fairly rigid foam rubber, cross linked polyethylene, or the like. It may be deposited on inner surface 24 of residual limb socket or shell 12. A good fit may be achieved by using a self-foaming material which is introduced into the inside 26 of residual limb socket or shell 12 and allowed to expand to a perfect natural fit while the residual limb of the user, suitably protected by an extremely thin film of plastic or the like wrapped around the residual limb is located in the residual limb socket or shell 12 at the desired location or if high temperature is necessary, a replica of the residual limb may be used.

Figure 3:
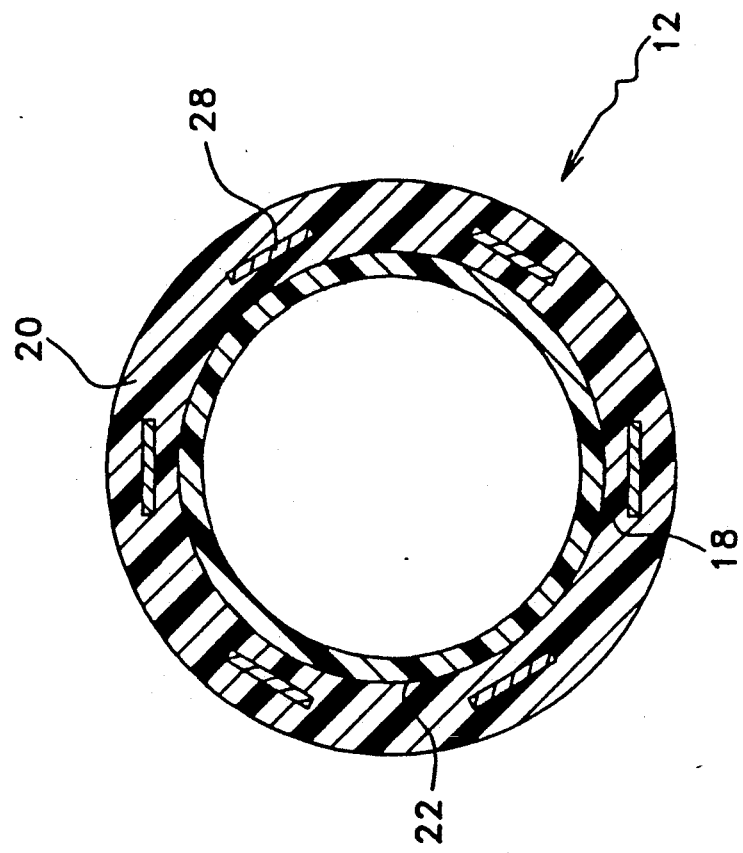
FIG. 3 is a cross-sectional view along lines 3—3 of FIG. 2.

Referring to FIGS. 2 and 3, residual limb socket or shell 12 is reinforced by a plurality of metal members which may take the form of strips 28.

Figure 4:
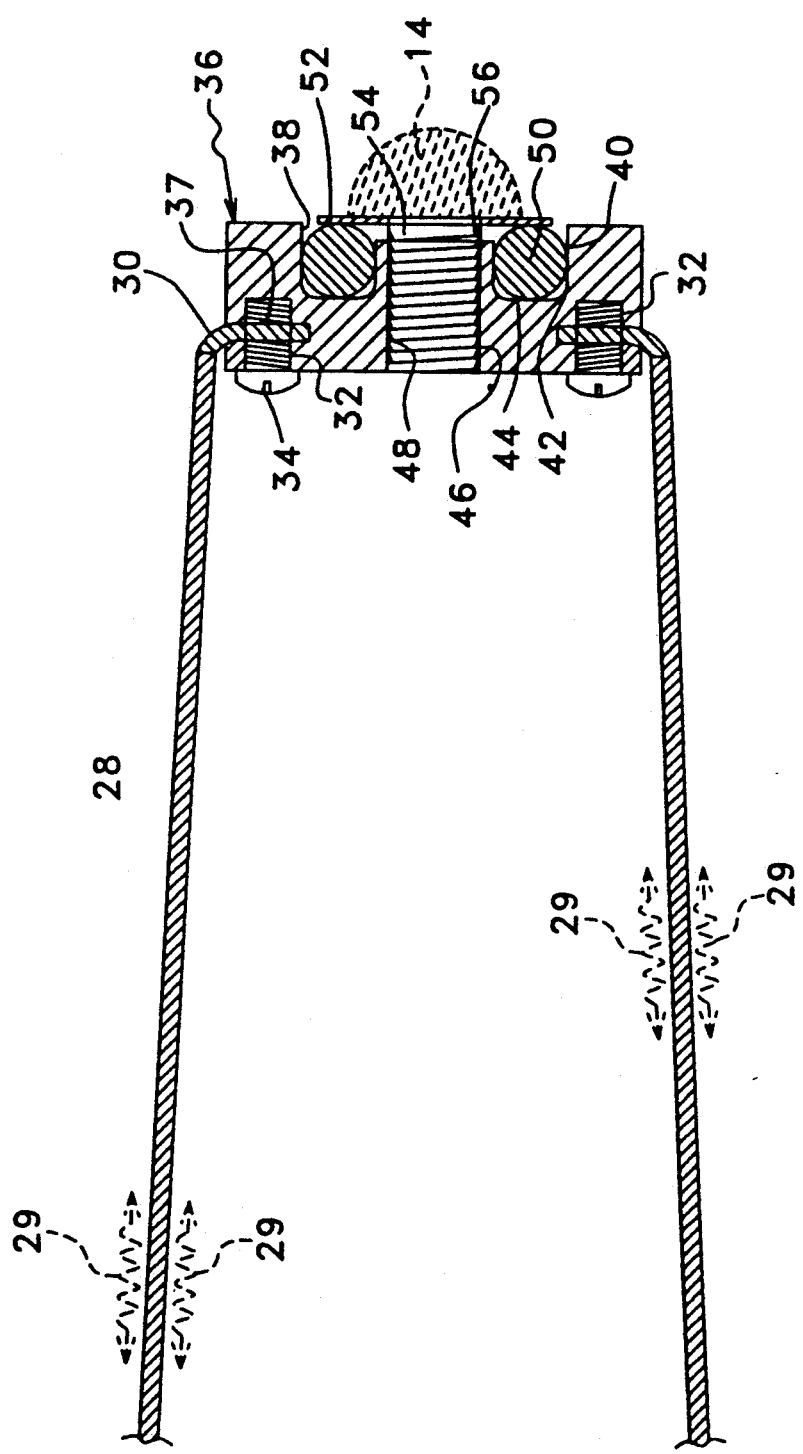
FIG. 4 is a detail of a portion of the apparatus shown in FIG. 2.

As illustrated in FIG. 4, each of the strips 28 terminate in a toe portion 30 which includes a hole 32 for receiving a securing screws 34.

Strips 28 are thus securely mounted to wrist 36 and may include a roughened or serrated surface 29, to enhance anchoring. Holes 37 are tapped to securely engage screws 34. Wrist 36 also includes an annular groove 38 defined by a long circumferential surface 40, a short circumferential surface 42 and a transverse surface 44.

A central hole 46 is defined in wrist 36. Central hole 46 is tapped and has threads 48, as illustrated most clearly in FIG. 4.

An elastic tension unit 50 made of rubber or other similar material and in the form of a rubber ring is disposed within annular groove 38, as illustrated in FIG. 4. A tension unit retainer 52 is positioned against tension unit 50 and is caused to forcibly bear against the elastic tension unit 50 by the prosthetic hand or hook 14, as illustrated by phantom lines in FIG. 4. More particularly, it is noted that hook 14 includes a threaded shank 54 which includes threads 56 which allows it to be threaded into hole 46 in wrist 36.

Typically, wrist 36 may be made of steel, such as stainless steel, or a strong alloy, bimetal or other similar material. Some plastics, with threaded metal fittings for the prosthetic unit attachment, may be used to further reduce weight. Likewise, screws 34 are, in accordance with the preferred embodiment, made of stainless steel. Strips 28 and retainer 52 are also stainless steel.

Figure 5:
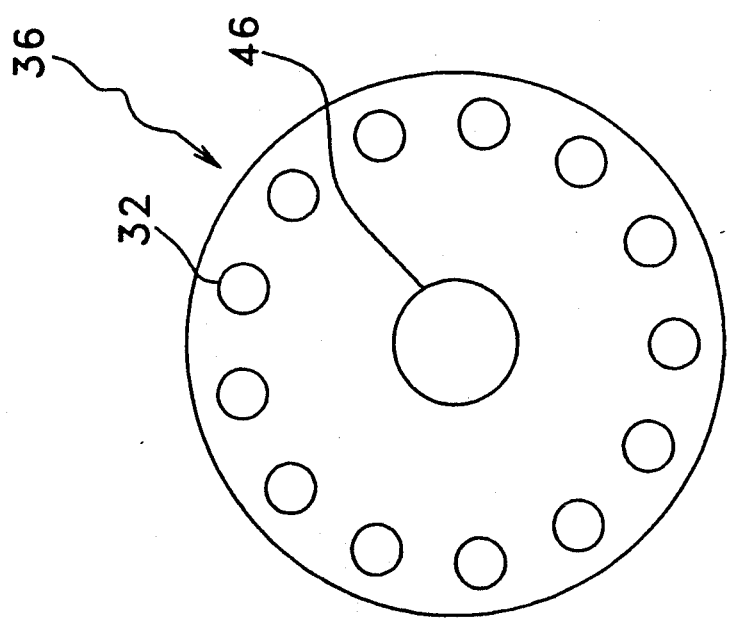
FIG. 5 is bottom plan view of the prosthetic wrist illustrated in FIG. 2.

While only six metal strips 28 are employed in the inventive prosthetic unit 10, 12 holes 32 are provided. The additional holes are provided for the purpose of reducing weight of the unit and, in special circumstances, providing means for attaching additional strips 28 to accommodate particular motions or needs of the user and/or relocating other strips for similar reasons. See FIG. 5.

While it is anticipated that the inventive prosthetic unit as shown in FIGS. 1-5 will have an extremely long life, it is possible that fatigue of the residual limb socket or shell 12 will necessitate replacement. Likewise, during the initial period of prosthetic use, when the prosthetic is worn, shrinking of the residual limb may require periodic replacement as frequently as every six months due to atrophy of the muscles or reduced swelling in the residual limb. Even though, to a certain extent, such changes in muscle size can be accommodated by changes in the foam fitting member 22, changing of the residual limb socket or shell 12 may be desirable.

Accordingly, in accordance with an alternative embodiment of the invention, the heads securing screws 34 may be exposed by forming the inner portion 18 of residual limb socket or shell 12 which will expose the heads of screws 34 as illustrated in phantom lines in FIG. 2.

Figure 6:
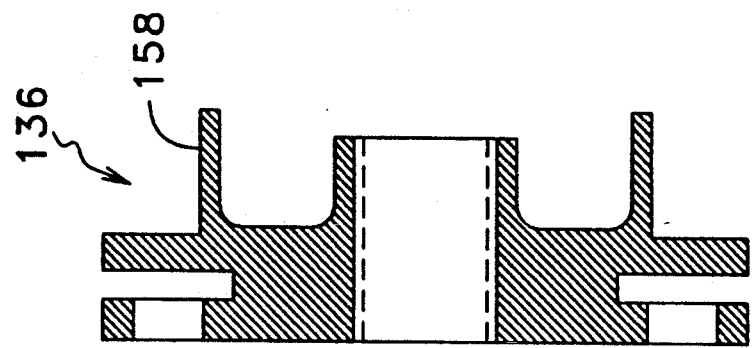
FIG. 6 is a cross-section view of a lightweight alternative prosthetic wrist unit constructed in accordance with the present invention.

An alternative embodiment is shown in FIG. 6. Generally, similar parts or parts performing analogous, corresponding or identical functions to those of the FIGS. 1 to 5 embodiment are numbered herein with numbers which differ from those of the earlier embodiment by multiples of one hundred.

In accordance with one preferred embodiment, strength can be maintained but weight reduced through the use of an alternative wrist 136 as illustrated in FIG. 6. More particularly, in wrist 136, annular portions are removed from the exposed corners of the wrist to expose an annular cutaway 158.

Figure 7:
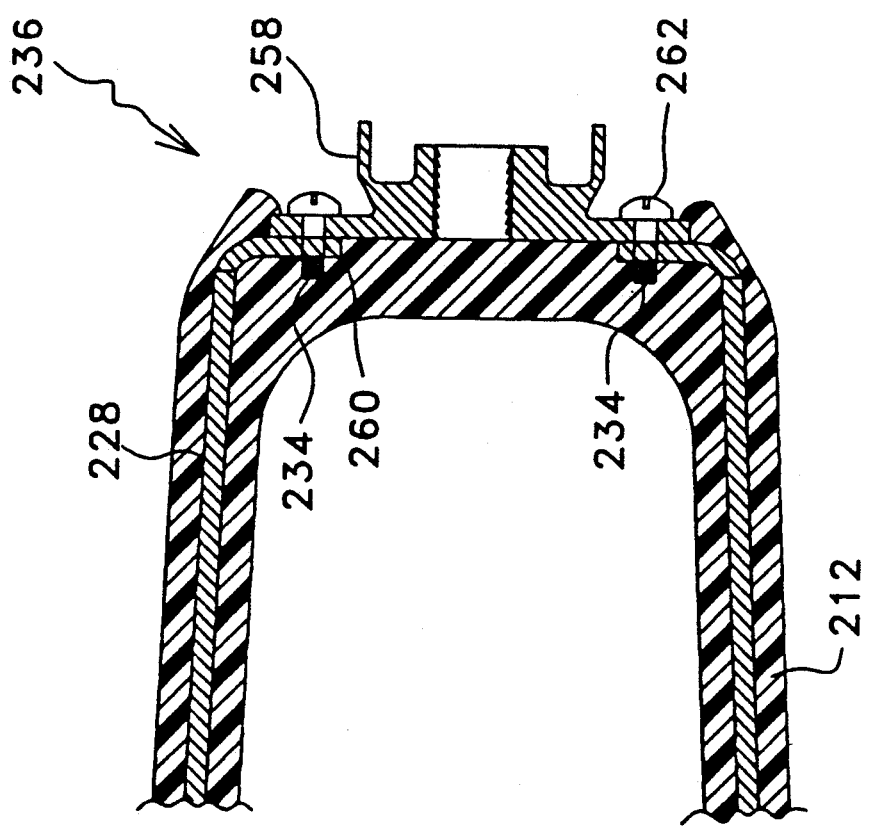
FIG. 7 is a cross-sectional view of the wrist unit of FIG. 6 in a prosthetic device.

Still yet another embodiment is illustrated in FIG. 7. Here the cutaway 258 in wrist 236 exposes screws 234 which threadingly engages tapped holes 260 in strips 228, as illustrated in FIG. 7. In accordance with this embodiment, the resinous material containing fiberglass or synthetic fiber reinforcing members which make up residual limb socket or shell 12 is formed to expose the heads 262 of screws 234 for easy replacement.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A prosthetic device comprising:
   a) a form-fitting residual limb socket or shell, comprising, at least in part, a lightweight resinous material, said form-fitting residual limb socket or shell defining a mounting end and an open end;
   b) a solid block-like mounting member having a longitudinal height and transverse width, the sizes of said height and width being of the same order of magnitude, said mounting member being secured to and rigidly engaging said mounting end and adapted to receive a conventional prosthetic coupling member; and
   c) a plurality of reinforcing support anchors secured to said mounting member and extending into said resinous material of said residual limb socket or shell, said anchors being secured to said mounting member at a plurality of points, each of said points being immediately proximate to corresponding points at which said anchors enter into said socket or shell.

2. A prosthetic device as in claim 1, wherein said support anchors each comprise an elongated support strip, said elongated support strip being positively locked to said mounting member.

3. A prosthetic device as in claim 2, wherein said elongated support strips have an irregular surface to enhance anchoring of said support strips to said resinous material.

4. A prosthetic device as in claim 3, wherein said irregular surface comprises serrations.

5. A prosthetic device as in claim 1, wherein said support anchors are secured to said mounting member by fasteners.

6. A prosthetic device as in claim 1, wherein said mounting member comprises:
   d) an external surface at an end of said mounting member;
   e) a sidewall;
   f) a hole defined within said mounting member and extending from said external surface; said hole being configured to receive a prosthetic coupling member.

7. A prosthetic device as in claim 6, wherein said hole is configured to define threads for receiving a threaded base member of said prosthetic coupling member and further comprises:
   h) a recess defined in the external surface of said mounting member, an elastic member disposed in said recess.

8. A prosthetic device as in claim 7, further comprising a pressure applying member having a hole disposed therein, said pressure applying member being positioned with said hole disposed over the hole defined in said mounting member and over said elastic member.

9. A prosthetic device as in claim 8, wherein said recess is an annular recess and said elastic member is a closed elastic ring.

10. A prosthetic device as in claim 1, wherein said support anchors are secured to said mounting member by bolts which are accessible to be screwed and unscrewed to allow easy replacement of said mounting member.

11. A prosthetic device as in claim 10, wherein said residual limb socket or shell has an inside form adapted to fit a human residual limb and an outside surface and wherein said bolts are accessible at said outside surface to allow easy replacement of said mounting member.

12. A prosthetic device as in claim 10, wherein said bolts are accessible from an inside surface of said socket or shell by removal of a soft liner material contained within said residual limb socket or shell.

13. A prosthetic device as in claim 1, further comprising a prosthetic hand secured to said mounting member.

14. A prosthetic device comprising:
   a) a form-fitting residual limb socket or shell, comprising, at least in part, a lightweight resinous material, said form-fitting residual limb socket or shell defining a mounting end and an open end;
   b) a metal mounting member secured to said mounting end and having a central hole disposed therein, said hole being threaded and adapted to receive a conventional prosthetic coupling member; and
   c) a plurality of metal support anchors secured to said mounting member and extending into said resinous material of said residual limb socket of shell, said anchors being secured to said mounting member at a plurality of points, each of said points being immediately proximate to corresponding points where said anchors enter into said socket or shell.

15. A prosthetic device as in claim 14, wherein said mounting member comprises a round cylindrically-shaped sidewall with a hole defined within said mounting member said hole being threaded to receive a prosthetic coupling member.

16. A prosthetic device as in claim 15, wherein said hole is configured to define threads for receiving a threaded base member of said prosthetic coupling member and further comprises a recess defined in the top of said mounting member, and an elastic member disposed in said recess.

17. A prosthetic device as in claim 16, further comprising a pressure applying member having a hole disposed therein, said pressure applying member being positioned with said hole disposed over the hole defined in said mounting member and over said elastic member.

18. A prosthetic device comprising:
   a) a form-fitting residual limb socket or shell, comprising, at least in part, a lightweight resinous material, said form-fitting residual limb socket or shell defining a mounting end and an open end;
   b) a solid block-like mounting member having a longitudinal height and transverse width, the sizes of said height and width being of the same order of magnitude, said mounting member being secured to said mounting end and adapted to receive a conventional prosthetic coupling member; and
   c) a plurality of metal support anchors secured to said mounting member and extending into said resinous material of said residual limb socket of shell, said anchors being secured to said mounting member at a plurality of points, each of said points being immediately proximate to corresponding points where said anchors enter into said socket or shell and said plurality of points and said corresponding points being positioned substantially at the radial periphery of said socket or shell.

19. A prosthetic device comprising:
   a) a form-fitting residual limb socket or shell, comprising, at least in part, a light-weight resinous material, said form-fitting residual limb socket or shell defining a mounting end and an open end;

b) a metal mounting member secured to said mounting end and adapted to receive a conventional prosthetic coupling member; and
c) a plurality of reinforcing support anchors secured to said mounting member and extending into said resinous material of said residual limb socket or shell, said anchors being secured to said mounting member at a plurality of points, each of said points being immediately proximate to corresponding points where said anchors enter into said socket or shell.

* * * * *